(12) United States Patent
Garrison et al.

(10) Patent No.: US 6,355,264 B1
(45) Date of Patent: *Mar. 12, 2002

(54) INSECT REPELLENT COMPOSITION

(75) Inventors: Mark Steven Garrison, Suffern, NY (US); Robert Edward Kalafsky, Ogdensburg, NJ (US)

(73) Assignee: Avon Products, Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/045,088

(22) Filed: Mar. 20, 1998

(51) Int. Cl.⁷ .......................... A01N 25/04; A01N 65/00
(52) U.S. Cl. .................. 424/405; 424/406; 424/407; 424/454; 424/59; 424/60; 424/78.02; 424/78.03; 424/750; 424/DIG. 10; 514/919
(58) Field of Search ................. 424/405, 406, 424/407, 484–488, 59, 60, 48, 467, 78.02–78.07, 736, 750, DIG. 10; 514/919, 937, 544

(56) References Cited

U.S. PATENT DOCUMENTS

| | | |
|---|---|---|
| 351,897 A | 11/1886 | Boyer et al. |
| 2,435,005 A * | 1/1948 | Huppke et al. ...... 424/DIG. 10 |
| 2,564,664 A | 8/1951 | Bartlett et al. |
| 3,186,912 A | 6/1965 | Beamer |
| 3,869,517 A | 3/1975 | Gradeff et al. |
| 4,049,828 A | 9/1977 | Cole |
| 4,164,561 A | 8/1979 | Hautmann |
| 4,256,600 A | 3/1981 | Lewis et al. |
| 4,449,987 A | 5/1984 | Lindauer |
| 4,774,081 A | 9/1988 | Flashinski et al. |
| 4,869,896 A * | 9/1989 | Coulton et al. ............... 424/45 |
| RE33,429 E * | 11/1990 | Abrutyn ..................... 514/847 |
| 5,227,406 A | 7/1993 | Beldock et al. |
| 5,298,250 A | 3/1994 | Lett et al. |
| 5,346,922 A | 9/1994 | Beldock et al. |
| 5,364,626 A | 11/1994 | Hasegawa et al. |
| 5,518,712 A | 5/1996 | Stewart |
| 5,518,736 A * | 5/1996 | Magdassi et al. ........... 424/451 |
| 5,565,208 A | 10/1996 | Vlasblom |
| 5,575,988 A | 11/1996 | Knowles, Jr. et al. |
| 5,621,013 A | 4/1997 | Beldock et al. |
| 5,648,398 A * | 7/1997 | Beldock et al. ............. 514/703 |
| 5,711,953 A | 1/1998 | Bassett |
| 5,716,602 A | 2/1998 | Ulck |
| 5,738,863 A * | 4/1998 | Saetrin et al. .............. 424/405 |

* cited by examiner

*Primary Examiner*—Neil Levy
(74) *Attorney, Agent, or Firm*—Ohlandt, Greeley, Ruggiero & Perle, LLP

(57) ABSTRACT

A novel insect repellent composition is provided that contains about 0.8 wt % to about 0.12 wt % oil of citronella, about 20 wt % to about 40 wt % emollient, and up to about 15 wt % $C_{12}$ to $C_{15}$ alkyl benzoate in an alcohol-containing vehicle suitable for topical application. The insect repellent compound may also contain a sunscreen and/or an ingredient that provides the insect repellent composition with water resistant/waterproof properties.

26 Claims, No Drawings

INSECT REPELLENT COMPOSITION

BACKGROUND OF THE INVENTION

1. Field of the Invention

The present invention relates to an insect repellent composition that achieves effective insect repellency with a relatively low concentration of a natural ingredient, oil of citronella. The present invention also relates to an insect repellent composition that provides ultraviolet (UV) sunscreen protection from both UVA and UVB radiation. In addition, the present invention relates to an insect repellent composition that provides ultraviolet protection and that is also water resistant/waterproof.

Insects are not only a nuisance to consumers who enjoy outdoor activities, but insects are also known to be carriers of disease. Mosquitoes, in particular, may act as vectors for diseases such as malaria and encephalitis.

In addition, the same outdoor daytime activities that expose consumers to disease-carrying insects, such as mosquitoes, also expose consumers to the damaging effects of UV exposure from the sun. Scientific literature has provided an abundance of documentation regarding the harm caused by extended, unprotected exposure to UV radiation. Consumers are also aware of the potential damage that results from extended, unprotected exposure to UV radiation and thus, prefer skin products that offer UV protection.

Consumers, who expose themselves to both insects and UV radiation during outdoor activity, often perspire or are exposed to water in other ways. As a result, it is important to provide an insect repellent composition that has water resistant/waterproof properties along with insect repellency and sunscreen activity.

N,N-diethyl-m-toluamide (DEET) is a presently available synthetic insect repellent that has demonstrated superior insect repellency in comparison to previous prior art natural insect repellents. However, there is concern that repeated DEET exposure may have harmful consequences. For example, possible DEET side effects are irritability, confusion, insomnia, and even seizures. For these reasons, caution is generally recommended with regard to the use of DEET as an insect repellent. This is especially true when DEET is applied to children, who are more susceptible to the potentially injurious effects of exposure to DEET.

Presently, there are products available that use floral or herbal extracts to provide insect repellency. There are even insect repellent products that contain oil of citronella. However, these prior art insect repellents have not been able to provide adequate insect repellency to meet consumer needs while primarily using a concentration of oil of citronella of about 0.08 wt % to about 0.12 wt %. (All percentages disclosed herein are weight percentages of the total composition unless otherwise specified.)

2. Description of the Prior Art

The use of oil of citronella in insect repellent products is known. However, high levels of oil of citronella have previously been required to provide the levels of insect repellency desired by consumers. Hence, oil of citronella is usually added to insect repellent products primarily as a fragrance, rather than primarily as an agent for insect repellent activity.

However, there have been previous attempts to produce an effective insect repellent product using only a relatively small concentration of oil of citronella. For example, U.S. Pat. No. 5,227,406 to Beldock et al. discloses insect repellents that contain at least 0.01% terpineol (preferably 0.06%), at least 0.01% citronella (oil of citronella, preferably 0.05%), at least 0.01% rhodinol extra (preferably 0.08%), and at least 0.01% geraniol (preferably 0.06%).

U.S. Pat. No. 5,346,922, also to Beldock et al., discloses insect repellents that contain at least 0.01% terpineol, at least 0.01% citronella (oil of citronella), and either at least 0.01% rhodinol extra or at least 0.01% geraniol. Preferably, the components are present at between 0.05% to 0.08%. Both the Beldock et al. '406 patent and the Beldock et al. '922 patent disclose that a sunscreen may be incorporated into the insect repellent compositions disclosed in each respective patent.

U.S. Pat. No. 5,621,013, also to Beldock et al., discloses insect repellents that contain approximately 0.05% citronella (oil of citronella), approximately 0.06% geraniol, approximately 0.08% to 0.5% crystalline 3,8 P-menthanediol, and approximately 0.06 terpineol and/or approximately 0.08% rhodinol (extra). The compound 3,8 P-menthanediol is a crystalline compound that is a naturally occurring component of a Chinese herb.

U.S. Pat. No. 5,648,398 discloses that a fragrance may be added to the insect repellent compositions disclosed in U.S. Pat. Nos. 5,227,406 and 5,346,922.

The insect repellent compositions disclosed by the Beldock et al. patent contain oil of citronella. Oil of citronella, a natural product, is composed of many chemical compounds, among which are terpineol, rhodinol and geraniol. The Beldock et al. repellent then augments oil of citronella with various combinations of additional amounts of terpineol, rhodinol, or geraniol. The result is that the finished repellent compositions disclosed by the Beldock et al. patents have a final concentration of terpineol, rhodinol or geraniol that is greater than that which is naturally present in oil of citronella.

SUMMARY OF THE INVENTION

It is an object of the present invention to provide an insect repellent composition that does not contain DEET and that is effective while utilizing only about 0.08 wt % to about 0.12 wt % oil of citronella.

It is also an object of the present invention to provide an insect repellent composition that provides average insect repellent protection time of greater than two hours.

It is another object of the present invention to provide an insect repellent composition that provides UVA/UVB protection.

It is still another object of the present invention to provide an insect repellent composition that both provides UVA/UVB protection and that is water resistant/waterproof.

It is further an object of the present invention to provide an insect repellent composition that may be used in a vehicle that contains alcohol as a primary ingredient and that contains little or no added water.

It is another object of the present invention to provide an insect repellent composition in a pleasant smelling, moisturizing, elegant and non-greasy alcohol-containing formulation.

It is yet a further object of the present invention to provide a liquid insect repellent composition that may be topically applied directly on human skin.

It is still yet a further object of the present invention to provide an insect repellent composition that may be topically applied either as a spray product or in a towlette.

To accomplish the foregoing, the present invention is, in brief summary, a topical composition that comprises about 0.08 wt % to about 0.12 wt % oil of citronella, about 20 wt % to about 40 wt % emollient and up to 15 wt % $C_{12}$ to $C_{15}$ alkyl benzoate (also known in the art as "$C_{12}$ to $C_{15}$ alcohols benzoate") in an alcohol-containing vehicle that is suitable for topical application. The composition may also include an UVA/UVB sunscreen. In addition to the UVA/UVB sunscreen, the composition may also be formulated to have water resistant/waterproof characteristics.

DETAILED DESCRIPTION OF THE PREFERRED EMBODIMENTS

The present invention is a composition that provides insect repellency. The composition includes oil of citronella, a emollient and certain $C_{12}$ to $C_{15}$ alkyl benzoate (also known as "$C_{12}$ to $C_{15}$ alcohols benzoate") in an alcohol-containing vehicle suitable for topical application.

The present invention is a composition that provides insect repellency that comprises about 0.08 wt % to 0.12 wt % oil of citronella, about 20 wt % to about 40 wt % emollient, and about up to 15 wt % $C_{12}$ to $C_{15}$ alkyl benzoate, with the remainder being an alcohol-containing vehicle suitable for topical application. All percentages set forth herein are percentages by weight of the total composition unless otherwise specified. Preferably, the insect repellent composition comprises about 0.09 wt % to about 0.11 wt % oil of citronella, about 25 wt % to 35 wt % emollient, and about 2 wt % to about 8 wt % $C_{12}$ to $C_{15}$ alkyl benzoate, with the remainder being an alcohol-containing vehicle suitable for topical application. More preferably, the insect repellent composition comprises between about 0.09 wt % to about 0.11 wt % oil of citronella, about 29 wt % to 31 wt % emollient, and about 4 wt % to about 6 wt % $C_{12}$ to $C_{15}$ alkyl benzoate, with the remainder being an alcohol-containing vehicle suitable for topical application. Most preferably, the insect repellent composition includes about 0.1 wt % oil of citronella, about 30 wt % emollient, and about 5 wt % $C_{12}$ to $C_{15}$ alkyl benzoate, with the remainder being an alcohol-containing vehicle suitable for topical application.

Although the resultant insect repellent composition has about 0.1 wt % oil of citronella, the resultant composition exhibits an unexpectedly high degree of insect repellent activity. The applicants do not wish to be bound by any theory, but it is believed that the combination of the oil of citronella, the emollient and the $C_{12}$ to $C_{15}$ alkyl benzoate produce a synergism that creates an effective insect repellent composition.

The emollient should have the following properties: good spreadability, chemical stability and miscibility with alcohol. Any emollient that exhibits the above-identified characteristics may be used to practice this invention. Examples of emollients contemplated for use in the insect repellent composition are fatty alcohols, fats and oils, hydrocarbons, ethers and esters. Specific examples of these types of emollients are listed below in Table 1. Preferably, the emollient is an ester. The preferred emollient ester may be isopropyl myristate, isopropyl palmitate, or a combination thereof. The most preferred emollient ester is isopropyl myristate.

Table 1

Examples of Emollients

Fatty Alcohols
octyldodecanol
cholesterol
cetyl alcohol
Fats and Oils
caprylic/capric triglyceride
hydrogenated palm oil
sesame oil
lanolin oil
Hydrocarbons
mineral oil
petrolatum
isoeicosane
Ethers
dicapryl ether
dimethyl isosorbide
Esters
isopropyl myristate
isopropyl palmitate
benzyl laurate
butyl octyl salicylate
butyl oleate
canola oil
$C_{12}$–$C_{15}$ alkyl octanoates
$C_{10}$–$C_{30}$ cholesterol/lanosterol esters
cetyl isononanoate
dicapryl adipate
dilauryl citrate
glyceryl monooleate
glycol dilaurate
isosorbide monolaurate
jojoba oil
Esters (Continued)
myristyl lactate
octyl palpitate
PEG-7 glyceryl cocoate
proylene glycol myristyl ether acetate
retinyl palmitate
tallow glycerides
tocopheryl acetate Any $C_{12}$ to $C_{15}$ alkyl benzoate known in the art may be used in the present invention. The most preferred $C_{12}$ to $C_{15}$ alkyl benzoate is available from Finetex under the registered trademark Finsolve TN.

The preferred vehicle for the insect repellent composition is alcohol-containing and contains little or no added water. More preferably, the vehicle contains no added water. The preferred vehicle contains about 20 wt % to about 50 wt % of any suitable cosmetic grade alcohol. Preferably, the cosmetic grade alcohol is a denatured alcohol. More preferably, the alcohol will be "specially denatured" (SD). The most preferred alcohol is SD alcohol 40 B.

The vehicle may also contain up to 50 wt % of a volatile silicone. The volatile silicone acts to improve the feel of the insect repellent composition against the skin. Preferably, the volatile silicone will comprise about 5 wt % to about 40 wt % of. the total weight of the composition. The preferred volatile silicone is cyclomethicone.

Preferably, the vehicle contains an antioxidant. The preferred antioxidant is butylated hydroxytoluene. The antioxidant is present from about 0.01 wt % to about 0.1 wt % of the total weight of the composition.

Preferably, the vehicle also contains a fragrance that will provide a pleasant smell to the present invention, but will not adversely affect the effectiveness of the insect repellent composition. More preferably, the fragrance will be present at about 0.1 wt % to about 1.0 wt % of the total weight of the composition. Most preferably, the insect repellent composition has about 0.5 wt % of a fragrance.

EXAMPLE

Nine human subjects were used to test the insect repellent properties of SAMPLE A.

| SAMPLE A | |
|---|---|
| oil of citronella | 0.1 wt % |
| isopropyl myristate | 30.0 wt % |
| $C_{12}$ to $C_{15}$ alkyl benzoate | 5.0 wt % |
| SD Alcohol 40 B | 32.0 wt % |
| cyclomethicone | 32.38 wt % |
| fragrance | 0.5 wt % |
| butylated hydroxytoluene | 0.02 wt % |

The test site selected for testing the efficacy of the insect repellent properties of SAMPLE A was Assateague National Sea Shore, which is known to have a significant population of the salt marsh mosquito, *Aedes sollicitans*. The untreated lower leg of the one subject served as the control.

The protocol utilized to prepare the test subjects for test conditions was as follows:

On the evening prior to the day of testing, the shoes of the test subjects and the control subject were treated with 0.5% permethrin. Since ticks are abundant in the testing area and are carriers of Lyme's disease, this precaution was instituted for the protection of the test subjects. The use of permethrin to protect the participants of the study does not negate the results of the test. It is known that permethrin is a contact insecticide that does not function as a volatile insect repellent. Accordingly, the presence of permethrin on the shoes of test subjects (and the control subject) will not affect the landing rate of insects on each subject and, thus the test results. The precautionary use of a tick repellent, such as permethrin, is common insect repellent testing protocol when ticks are known to be present in the testing area.

Prior to arriving at the test site, the subjects (both test subjects and the control) washed the test areas, which were either on their legs or on their forearms, with IVORY® soap. After arrival at the test site, Sample A was then applied to the test areas of the test subjects.

Biting pressure was determined by the insect landing rate on the test area of the control subject. If the control subject obtained an insect landing rate of at least 1 to 10 per minute, the biting pressure was deemed acceptable to continue testing at that particular testing site.

The efficacy of Sample A was evaluated by continuous exposure of the test area of the test subjects. The test area was exposed until three bites occurred within one hour (each bite being required to occur within 30 minutes of one of the other two bites) or until four hours elapsed, whichever occurred first.

Sample A was found to provide an average insect repellent protection time that was greater than two hours.

Thus, experimentation has demonstrated that the insect repellent composition of the present invention provides significant insect repellent properties while utilizing only about 0.1 wt % oil of citronella in conjunction with about 30 wt % of a emollient and about 5 wt % of $C_{12}$ to $C_{15}$ alkyl benzoate.

In a second embodiment of the present invention, the insect repellent composition includes a sunscreen. The sunscreen provides UVA/UVB protection. The sunscreen may be any such sunscreen known in the art that can used with a topical alcohol-containing vehicle. In addition, a combination of two or more sunscreens may be used. Among the sunscreens that may be used in the insect repellent composition are sunscreens from the following categories (or their derivatives): para-aminobenzoic acid ("paba"), benzophenone, cinnamic acid, cinnamate esters, camphor, anthranillic acids, salicylic acids, benzotriazole, oxazoles, urocanic acids, dibenzoyl methanes, benzoic acid, diphenyl acrylates, gallic acids, titanium dioxides, zinc oxides and sunscreens containing a propane 1,3 dione moiety.

Examples of some sunscreens that may be used are as follows: octyl dimethyl paba, benzophenone-3, octyl methoxy cinnamate, terephthalylidene dicamphor sulfonic acid (available under the trademark Mexoryl SX), menthyl anthraniliate, octyl salicylate, benzotriazole, 5-methyl 2 phenylbenzoxazole, ethyl urocanate, butyl methoxydibenzoylmenthane (available under the trademark Parsol 1789), benzyl salicylate, 2-ethylhexyl 2-cyano-3,3, diphenylacrylate, digalloyl tristearate, titanium dioxide, zinc oxide and 1-cumenyl-3-phenylpropane 1,3-dione. The preferred sunscreens are octyl methoxy cinnamate, octyl salicylate, octocrylene and butyl methoxydibenzoylmethane. As indicated above, butyl methoxydibenzoylmethane is sold by Hoffman-LaRoche under the registered trademark Parsol 1789.

Preferably, a composition of the second embodiment of the present invention includes about 5 wt % to about 10 wt % octyl methoxy cinnamate, up to about 10 wt % octyl salicylate, up to about 15 wt % octocrylene, and up to 5 wt % butyl methoxy-dibenzoylmethane. Most preferably, a composition of the second embodiment includes about 7.5 wt % octyl methoxy cinnamate, about 5 wt % octyl salicylate, about 10 wt % octocrylene, and about 3 wt % butyl methoxydibenzoylmethane. An example of a preferred composition of the second embodiment of the present invention is as follows:

EXAMPLE 1

| oil of citronella | 0.1% |
|---|---|
| isopropyl myristate | 30.0 |
| $C_{12}$ to $C_{15}$ alkyl benzoate | 5.0 |
| SD Alcohol 40 B | 32.0 |
| cyclomethicone | 9.88% |
| fragrance | 0.5% |
| butylated hydroxytoluene | 0.02% |
| octyl methoxy cinnamate | 7.5% |
| octyl salicylate | 5.0 |
| octocrylene | 10.0% |
| butyl methoxydibenzoylmethane (Parsol 1789) | 3.0% |

In a third embodiment of the present invention, the insect repellent composition contains a sunscreen and an ingredient that provides water-resistance/waterproof properties. Any water resistant/waterproof ingredient which is suitable for use in topical alcohol-containing vehicles may be used. The preferred water resistant/waterproof ingredients are polyvinyl pyrrolidone (PVP) copolymers and their derivatives and acrylates/octyl acrylamide copolymers (sold by National Starch under the tradename Dermacryl). Further examples of suitable water resistant/waterproof ingredients that may be used are: PVP eicosene, PVP hexadecene and tricontonyl PVP. Preferably, a composition of the third embodiment of the present invention includes up to about 10 wt % of the water resistant/waterproof ingredient. More preferably, a composition of the third embodiment of the present invention includes up to about 5 wt % of the agent water resistant/waterproof agent. Most preferably, a composition of the third preferred embodiment of the present invention includes up to about 3 wt % of the water resistant/waterproof agent. An example of a preferred composition of this third embodiment is as follows:

EXAMPLE 2

| | |
|---|---|
| oil of citronella | 0.1% |
| isopropyl myristate | 30.0% |
| $C_{12}$ to $C_{15}$ alkyl benzoate | 5.0% |
| SD Alcohol 40 B | 32.0% |
| cyclomethicone | 8.38% |
| fragrance | 0.5% |
| butylated hydroxytoluene | 0.02% |
| octyl methoxy cinnamate | 7.5% |
| octyl salicylate | 5.0% |
| octocrylene | 10.0% |
| butyl methoxydibenzoylmethane (Parsol 1789 ®) | 3.0% |
| acrylates/ octyl acrylamide copolymer | 1.5% |

Each of the above three embodiments of the insect repellent composition, as exemplified by Sample A, Example 1 and Example 2, may be applied topically to the consumer's skin directly. Also, any of the above described three embodiments of the present invention may be applied to the consumer's skin as a spray product. As another alternative, any of three embodiments of the present invention may be incorporated into a towlette. The consumer may then topically apply the insect repellent composition by rubbing the towlette against the consumer's skin.

The present invention is not limited to the examples illustrated above, as it is understood that one ordinarily skilled in the art would be able to utilize substitutes and equivalents without departing from the present invention.

What is claimed is:

1. An insect repellent composition suitable for topical application, comprising:
    an oil of citronella;
    an emollient;
    a $C_{12}$ to $C_{15}$ alkyl benzoate;
    an alcohol-containing vehicle; and
    an ingredient selected from the group consisting of a sunscreen, a fragrance, an antioxidant, a water-resistance/waterproofing agent, a feel modifying agent, and mixtures thereof.

2. The insect repellent composition of claim 1, wherein the oil of citronella is present from about 0.08 wt % to about 0.12 wt %.

3. The insect repellent composition of claim 1, wherein the emollient is present from about 20 wt % to about 40 wt %.

4. The insect repellent composition of claim 1, wherein the emollient is selected from the group consisting of: fatty alcohols, fats, oils, hydrocarbons, ethers thereof, esters thereof, and mixtures thereof.

5. The insect repellent composition of claim 4, wherein the emollient is selected from the group consisting of: isopropyl myristate, isopropyl palmitate, and a mixture thereof.

6. The insect repellent composition of claim 1, wherein the $C_{12}$ to $C_{15}$ alkyl benzoate is present from about 2 wt % to about 15 wt %.

7. The insect repellent composition of claim 1, wherein the alcohol-containing ingredient includes a cosmetic grade alcohol.

8. The insect repellent composition of claim 1, wherein the ingredient is the sunscreen.

9. The insect repellent composition of claim 8, wherein the sunscreen is selected from the group consisting of: octyl salicylate, octocrylene, butyl methoxydibenzoylmethane, para-aminobenzoic acid, benzophenones, cinnamic acid, cinnamate esters, camphor, anthranillic acids, salicylic acids, benzotriazole, oxazoles, urocanic acids, dibenzoyl methanes, benzoic acid, diphenyl acrylates, gallic acids, titanium dioxides, zinc oxides, sunscreens containing a propane 1,3 dione moiety, octyl dimethyl paba, benzophenone-3, octyl methoxy cinnamate, terephthalylidene dicamphor sulfonic acid, menthyl anthraniliate, benzotriazole, 5-methyl 2 phenylbenzoxazole, ethyl urocanate, benzyl salicylate, 2-ethylhexyl 2-cyano-3,3, diphenylacrylate, digalloyl tristearate, 1-cumenyl-3-phenylpropane 1,3-dione, and mixtures thereof.

10. The insect repellent composition of claim 8, wherein the sunscreen is selected from the group consisting of octyl methoxy cinnamate, octyl salicylate, octocrylene and butyl methoxydibenzoylmethane, and mixtures thereof.

11. The insect repellent composition of claim 1, wherein the ingredient is the fragrance.

12. The insect repellent composition of claim 1, wherein the ingredient is the antioxidant.

13. The insect repellent composition of claim 1, wherein the antioxidant is butylated hydroxytoluene.

14. The insect repellent composition of claim 1, wherein the ingredient is the water-resistant/waterproofing agent.

15. The insect repellent composition of claim 14, wherein water-resistant/waterproofing agent is selected from the group consisting of polyvinyl pyrrolidone copolymers, acrylates/octyl acrylamide copolymers, derivatives thereof, and mixtures thereof.

16. The insect repellent composition of claim 1, wherein the ingredient is the feel modifying agent.

17. The insect repellent composition of claim 16, wherein the feel modifying agent is a volatile silicone and present from about 5 wt % to about 50 wt %.

18. The insect repellent composition of claim 17, wherein the volatile silicone is a cylclomethicone.

19. The insect repellent composition of claim 1, wherein the ingredient is a mixture of the sunscreen and the water-resistance/waterproofing agent.

20. The insect repellent composition of claim 1, wherein the ingredient is a mixture of:
    the sunscreen;
    the fragrance;
    the antioxidant;
    the feel modifying agent; and
    the water-resistance/waterproofing agent.

21. The insect repellent composition of claim 1, wherein the oil of citronella is present from about 0.09 to about 0.11 wt. %.

22. The insect repellent composition of claim 1, wherein the composition is applied for insect repellency.

23. The insect repellent composition of claim 1, wherein the ingredients is three or more of the ingredients.

24. The insect repellent composition of claim 1, wherein the alcohol-containing vehicle is substantially non-absorbent/adsorbent and substantially non-gelling.

25. An insect repellent composition suitable for topical application, consisting essentially of:

oil of citronella;

an emollient;

a $C_{12}$ to $C_{15}$ alkyl benzoate;

an alcohol-containing vehicle; and an ingredient selected from the group consisting of a sunscreen, a fragrance, an antioxidant, a water-resistance/waterproofing agent, a feel modifying agent, and mixtures thereof.

26. An insect repellent composition suitable for topical application, consisting of:

oil of citronella;

an emollient;

a $C_{12}$ to $C_{15}$ alkyl benzoate;

an alcohol-containing vehicle; and an ingredient selected from the group consisting of a sunscreen, a fragrance, an antioxidant, a water-resistance/waterproofing agent, a feel modifying agent, and mixtures thereof.

* * * * *